US012805847B2

(12) United States Patent
Rajguru et al.

(10) Patent No.: US 12,805,847 B2
(45) Date of Patent: Nov. 24, 2026

(54) INTRALUMINAL ULTRASOUND DIRECTIONAL GUIDANCE AND ASSOCIATED DEVICES, SYSTEMS, AND METHODS

(71) Applicant: VOLCANO CORPORATION, San Diego, CA (US)

(72) Inventors: Nikhil Sreedhar Rajguru, San Diego, CA (US); Alessandra Di Tullio, Best (NL); Anuja Nair, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 33 days.

(21) Appl. No.: 16/663,412

(22) Filed: Oct. 25, 2019

(65) Prior Publication Data

US 2020/0129159 A1 Apr. 30, 2020

Related U.S. Application Data

(60) Provisional application No. 62/751,167, filed on Oct. 26, 2018.

(51) Int. Cl.
*A61B 8/00* (2006.01)
*A61B 8/12* (2006.01)

(52) U.S. Cl.
CPC .............. *A61B 8/5292* (2013.01); *A61B 8/12* (2013.01); *A61B 8/445* (2013.01); *A61B 8/4461* (2013.01); *A61B 8/463* (2013.01)

(58) Field of Classification Search
CPC ......... A61B 8/5292; A61B 8/12; A61B 8/445; A61B 8/4461; A61B 8/463; A61B 8/0891; A61B 8/461
See application file for complete search history.

(56) References Cited

U.S. PATENT DOCUMENTS

| | | | | | |
|---|---|---|---|---|---|
| 6,027,451 | A * | 2/2000 | McGee | A61B 8/0833 600/463 |
| 6,099,471 | A * | 8/2000 | Torp | G01S 7/52042 600/443 |
| 6,148,095 | A * | 11/2000 | Prause | A61B 6/504 600/467 |
| 6,200,268 | B1 | 3/2001 | Vince | |
| 6,381,350 | B1 | 4/2002 | Klingensmith | |
| 7,074,188 | B2 | 7/2006 | Nair | |
| 7,175,597 | B2 | 2/2007 | Vince | |

(Continued)

FOREIGN PATENT DOCUMENTS

| | | |
|---|---|---|
| JP | 2004121488 A | 4/2004 |
| WO | 2019175004 A1 | 9/2019 |

*Primary Examiner* — Andrew W Begeman

(57) ABSTRACT

Disclosed is an intraluminal ultrasound imaging system, including a processor in communication with an intraluminal ultrasound imaging catheter, and configured to receive a plurality of intraluminal ultrasound images obtained by the intraluminal ultrasound imaging catheter while the intraluminal ultrasound imaging catheter is moved through a body lumen of a patient. The processor is further configured to determine an orientation of each of the plurality of intraluminal ultrasound images, and display an intraluminal ultrasound image of the plurality of intraluminal ultrasound images, and a directionality indicator identifying the orientation of the intraluminal ultrasound image.

24 Claims, 10 Drawing Sheets

(56) References Cited

U.S. PATENT DOCUMENTS

| | | | | |
|---|---|---|---|---|
| 7,215,802 | B2 | 5/2007 | Klingensmith | |
| 7,359,554 | B2 | 4/2008 | Klingensmith | |
| 7,463,759 | B2 | 12/2008 | Klingensmith | |
| 7,846,101 | B2 | 12/2010 | Eberle | |
| 7,930,014 | B2 | 4/2011 | Huennekens | |
| 8,298,147 | B2 | 10/2012 | Huenneken | |
| 8,777,855 | B2 | 7/2014 | Hyun | |
| 2002/0188225 | A1* | 12/2002 | White | A61B 8/4461 600/585 |
| 2003/0065265 | A1* | 4/2003 | Jackson | G01S 7/52068 600/443 |
| 2006/0241445 | A1* | 10/2006 | Altmann | A61B 8/12 600/443 |
| 2006/0241465 | A1* | 10/2006 | Huennekens | A61B 5/06 600/458 |
| 2008/0004530 | A1* | 1/2008 | Feldman | A61B 8/5238 600/467 |
| 2008/0234582 | A1* | 9/2008 | Nair | A61B 8/4488 600/443 |
| 2009/0005679 | A1* | 1/2009 | Dala-Krishna | A61B 8/483 600/437 |
| 2013/0072795 | A1* | 3/2013 | Mo | A61B 8/14 600/443 |
| 2014/0236207 | A1* | 8/2014 | Makower | A61F 2/2493 606/185 |
| 2015/0073279 | A1* | 3/2015 | Cai | A61B 8/0891 600/463 |
| 2016/0000401 | A1* | 1/2016 | Mienkina | A61B 8/5223 600/443 |
| 2019/0008480 | A1* | 1/2019 | Gerard | A61B 8/5223 |
| 2019/0117191 | A1* | 4/2019 | Hoffman | A61B 5/0084 |
| 2019/0282199 | A1 | 9/2019 | Merritt | |
| 2020/0397294 | A1* | 12/2020 | Wissel | A61B 5/065 |

* cited by examiner

INTRALUMINAL ULTRASOUND DIRECTIONAL GUIDANCE AND ASSOCIATED DEVICES, SYSTEMS, AND METHODS

CROSS REFERENCE TO RELATED APPLICATIONS

This application claims priority to, and the benefit of, U.S. Provisional Patent Application No. 62/751,167, filed Oct. 26, 2018, which is incorporated by reference herein in its entirety.

TECHNICAL FIELD

The subject matter described herein relates to a system for medical imaging. In particular, the disclosed system provides navigation and measurement aids to facilitate acquisition and display of peripheral intravascular ultrasound or IVUS images. This system has particular but not exclusive utility for diagnosis and treatment of vascular diseases.

BACKGROUND

Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object that may be placed in a vessel or lumen to hold the vessel or lumen open to a particular diameter. In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

IVUS images do not incorporate inherent directional cues as to how the image is aligned within a human body. Even if an imaging catheter has a known "12-o-clock" position along its circumference, this is of little help to clinicians if the orientation of the catheter is unknown or changing. Many clinician tasks during a typical intravascular imaging procedure (e.g., an IVUS pullback) are time consuming, require specific actions to be taken by the clinician, require the clinician to deduce the orientation of images, or must be performed in a particular (typically memorized) sequence. Furthermore, in the absence of clear understanding of the orientation of disease within the intraluminal images, clinicians may take a long time figuring out where to treat or ablate, or may need to switch back and forth repeatedly between different imaging modalities to determine directionality, or may have to determine directionality by interpreting the surrounding anatomy.

Thus, while performing vascular procedures, clinicians often resort to manual methods to align themselves to the anatomy that is under study—for example, marking on a venogram, interpreting displayed images and surrounding anatomical markers that show up on the screen, etc.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for supplying position and orientation information of an intravascular imaging probe to a clinician or other user, along with automated analysis of anatomical features, and step-by-step instructions for the clinician to perform a desired procedure. According to at least one embodiment of the present disclosure, a system is provided for determining the orientation of intraluminal images, performing automated measurements of lumens, displaying an intraluminal imaging probe on a co-registered roadmap image, and supplying step-by-step instructions to a clinician or other user. The system is hereinafter referred to as an intraluminal directional guidance system.

The intraluminal directional guidance system disclosed herein has particular, but not exclusive, utility for intraluminal ultrasound imaging procedures. One general aspect of the intraluminal directional guidance system includes an intraluminal ultrasound imaging system, including: a processor circuit configured for communication with an intraluminal ultrasound imaging catheter, where the processor circuit is configured to: receive a plurality of intraluminal ultrasound images obtained by the intraluminal ultrasound imaging catheter while the intraluminal ultrasound imaging catheter is moved through a body lumen of a patient; determine an orientation of each of the plurality of intraluminal ultrasound images; output, to a display in communication with the processor circuit, a screen display including: an intraluminal ultrasound image of the plurality of intraluminal ultrasound images; and a directionality indicator identifying the orientation of the intraluminal ultrasound image. Other embodiments of this aspect include corresponding computer systems, apparatus, and computer programs recorded on one or more computer storage devices, each configured to perform the actions of the methods.

Implementations may include one or more of the following features. The system where the processor circuit is configured to: output, via the screen display, the plurality of intraluminal ultrasound images; and change the directionality indicator to identify the orientation of a corresponding one of the plurality of intraluminal ultrasound images. The system where the processor circuit is configured to output, via the screen display, the plurality of intraluminal ultrasound images such that each of the plurality of intraluminal ultrasound images is rotated in the screen display based on the determined orientation, where the directionality indicator includes the same orientation in the screen display for the plurality of intraluminal ultrasound images. The system where the directionality indicator includes a direction relative to at least one of the body lumen or the patient. The system where the direction relative to the patient includes at least one of an anterior direction, a posterior direction, a medial direction, or a lateral direction. The system further including a user interface in communication with the processor circuit, where the processor circuit is configured to receive a user input via the user interface. The system where the processor circuit is configured to reorient at least one of the intraluminal ultrasound image or the directionality indicator in the screen display, in response to the user input. The system where the processor circuit is configured to: perform an enhancement of the intraluminal ultrasound image, in response to the user input; and modify the intraluminal ultrasound image in the screen display based on the enhancement. The system where the enhancement includes a change to at least one of contrast, gain, focus, or brightness of the intraluminal ultrasound image. The system where the processor circuit is configured to: perform an automatic measurement of the body lumen based on the intraluminal ultrasound image; and output the automatic measurement via the screen display. The system where the automatic measurement includes at least one of an area, a diameter, a length, or a compression percentage. The system where the screen display further includes: an external view of the body lumen. The system where the screen display further includes an indicator identifying a location of the intraluminal ultrasound image along a length of the body lumen in the external view. The system where the screen display further includes an instructional pane displaying at least one of status information about the system, instructions for operating the system, or instructions for moving the intraluminal ultrasound imaging catheter through the body lumen. The system further including: the intraluminal ultrasound imaging catheter. The system where the processor circuit is configured to identify at least one anatomical landmark in the plurality of intraluminal ultrasound images, and where the processor circuit determining the orientation is based on the at least one anatomical landmark. Implementations of the described techniques may include hardware, a method or process, or computer software on a computer-accessible medium.

One general aspect includes an intraluminal ultrasound imaging method, including: receiving, at a processor circuit in communication with an intraluminal ultrasound imaging catheter, a plurality of intraluminal ultrasound images obtained by the intraluminal ultrasound imaging catheter while the intraluminal ultrasound imaging catheter is moved through a body lumen of a patient; determining, by the processor circuit, an orientation of each of the plurality of intraluminal ultrasound images; and outputting, to a display in communication with the processor circuit, a screen display including: an intraluminal ultrasound image of the plurality of intraluminal ultrasound images; and a directionality indicator identifying the orientation of the intraluminal ultrasound image. Other embodiments of this aspect include corresponding computer systems, apparatus, and computer programs recorded on one or more computer storage devices, each configured to perform the actions of the methods.

One general aspect includes an intravascular ultrasound imaging system for use in peripheral vasculature, the system including: an intravascular ultrasound imaging catheter configured to obtain a plurality of intravascular ultrasound images while the intravascular ultrasound imaging catheter is moved through a peripheral blood vessel of a patient; a processor circuit configured for communication with the intravascular ultrasound imaging catheter, where the processor circuit is configured to: receive the plurality of intravascular ultrasound images obtained by the intravascular ultrasound imaging catheter; identify at least one anatomical landmark in the plurality of intravascular ultrasound images; determine an orientation of each of the plurality of intravascular ultrasound images based on the at least one anatomical landmark; output, to a display in communication with the processor circuit, a screen display including: an intravascular ultrasound image of the plurality of intravascular ultrasound images; and a directionality indicator identifying the orientation of the intravascular ultrasound image. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the intraluminal directional guidance system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
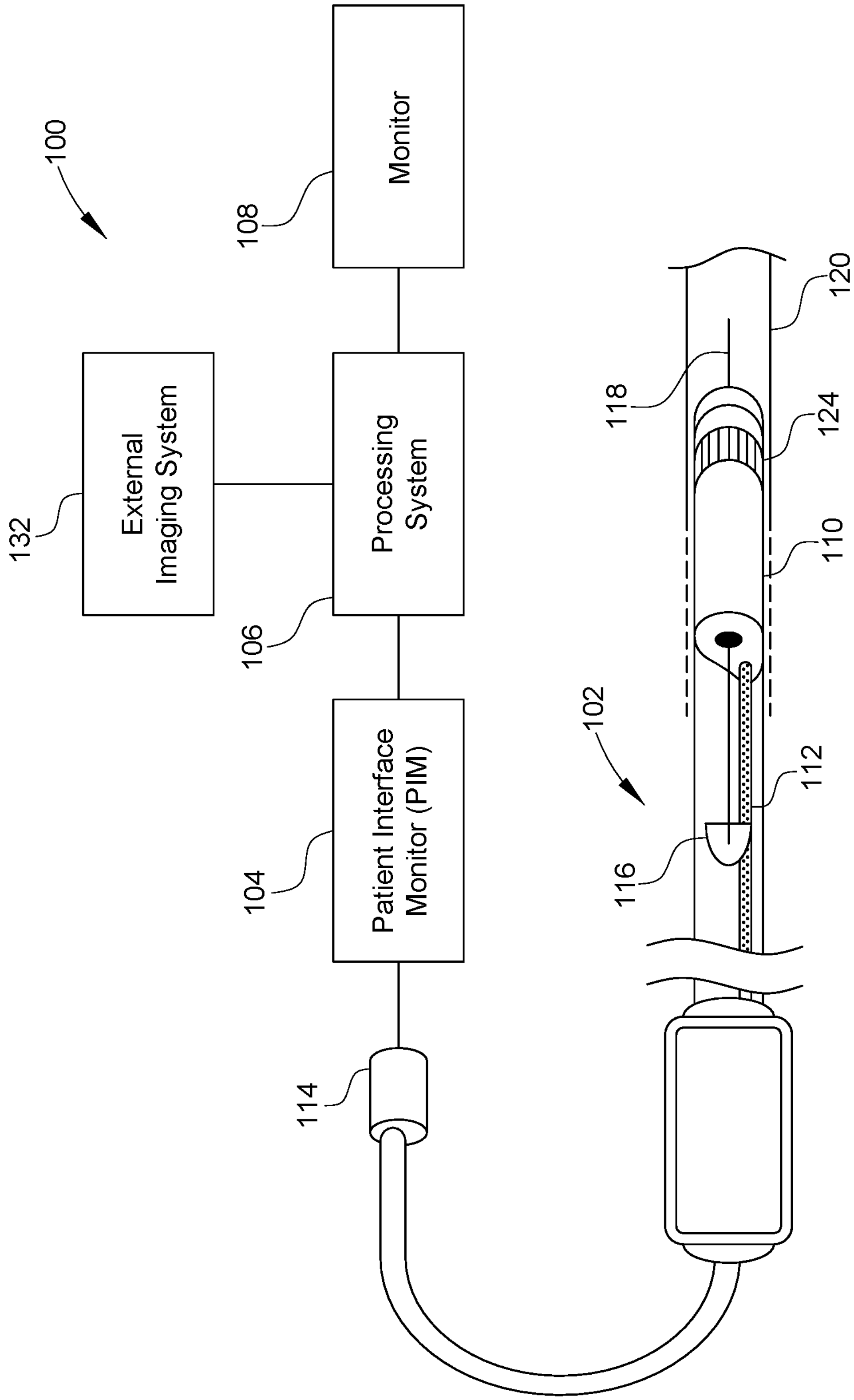
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes guidance and navigation aids for acquisition and display of peripheral intravascular ultrasound or IVUS images. In accordance with at least one embodiment of the present disclosure, a system is provided for determining the orientation of intraluminal images, performing automated measurements of lumens, displaying an intraluminal imaging probe on a co-registered roadmap image, and supplying step-by-step instructions to a clinician or other user. This system is hereinafter referred to as an intraluminal directional guidance system.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. 62/642,847, filed Mar. 14, 2018 (and a Non-Provisional application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional application filed therefrom on Mar. 15, 2019 as U.S. Ser. No. 16/354,970), each of which is hereby incorporated by reference in its entirety as though fully set forth herein.

The present disclosure helps overcome the barriers of expertise in system handling, image interpretation and extended workflows by providing ways to present the user with directional information, and/or automatically align the image being shown to the directional information such as—anterior/posterior, and medial/lateral. This helps in training, and also aligning the mind with the anatomy for guidance during vascular procedures such as atherectomy. The present disclosure provides live directional information on the screen based on automatic analysis of anatomical markers, and/or with minimal user intervention, during vascular procedures, without the help of fluoroscopic images. Accordingly, the present disclosure substantially aids a clinician in orienting, navigating, and guiding an intravascular imaging probe or intraluminal imaging probe within a vessel or lumen of a patient, by providing directional navigation information during intraluminal medical imaging procedures. The directional navigation information may include directionality indicators, automatic measurement tools, step by step navigation or operating instructions, and co-registered vessel maps showing the position of the probe within a patient's anatomy. The directional navigation information may be edited or corrected by a user in real time or near real time, to reorient the images or direction indicators to the user input. Implemented on a medical imaging console (e.g., an intraluminal imaging console) in communication with a medical imaging sensor (e.g., an intraluminal ultrasound sensor), the intraluminal directional guidance system disclosed herein provides both time savings and an improvement in the quality of captured images. This improved imaging workflow transforms raw imaging data into annotated roadmaps, anatomical measurements, and step-by-step instructions for a clinician to perform a given procedure. This occurs without the normally routine need to change manual settings, activate manual features, memorize procedures, or refer to procedure manuals. This unconventional approach improves the functioning of the medical imaging console and sensor, by permitting more efficient workflow.

The intraluminal directional guidance system may be implemented as a set of logical branches and mathematical operations, whose outputs are viewable on a display, and operated by a control process executing on a processor that accepts user inputs from a keyboard, mouse, or touchscreen interface, and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment). Image processing of intraluminal medical images may occur while the images or being captured, or later during a review or playback mode. Different image processing parameters control different visual aspects of the processed medical image.

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

In some embodiments, the intraluminal directional guidance system includes screen displays that provide a clinician with guidance during an IVUS pullback in peripheral vasculature, or other intravascular imaging procedure. The screen displays provide: on-demand smart directionality indications, live measurements, and guidance (e.g., displayed text) on how a user should perform the steps in an imaging workflow.

These descriptions are provided for exemplary purposes only, and should not be considered to limit the scope of the intraluminal directional guidance system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the intraluminal directional guidance system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of the displays or visualizations shown in FIGS. 5-7.

The external imaging system 132 can be configured to obtain x-ray, radiographic, angiographic/venographic (e.g., with contrast), and/or fluoroscopic (e.g., without contrast) images of the body of patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

In some embodiments, the external imaging system 132 is an extraluminal imaging system. Screen displays incorporating information from the external imaging system may include raw images, processed images, or stylized diagrams or cartoons of the body lumen. The processing system 106 can be in communication with an external imaging device (e.g., Mill, CT, x-ray such as angiography and/or fluoroscopy), and a displayed external or extraluminal view can be an external image itself or a 2D/3D reconstruction of the body lumen based on the external image, and in some embodiments the external or extraluminal view may include an indicator identifying a location of the intraluminal ultrasound image along a length of the body lumen in the external or extraluminal view.

Figure 2:
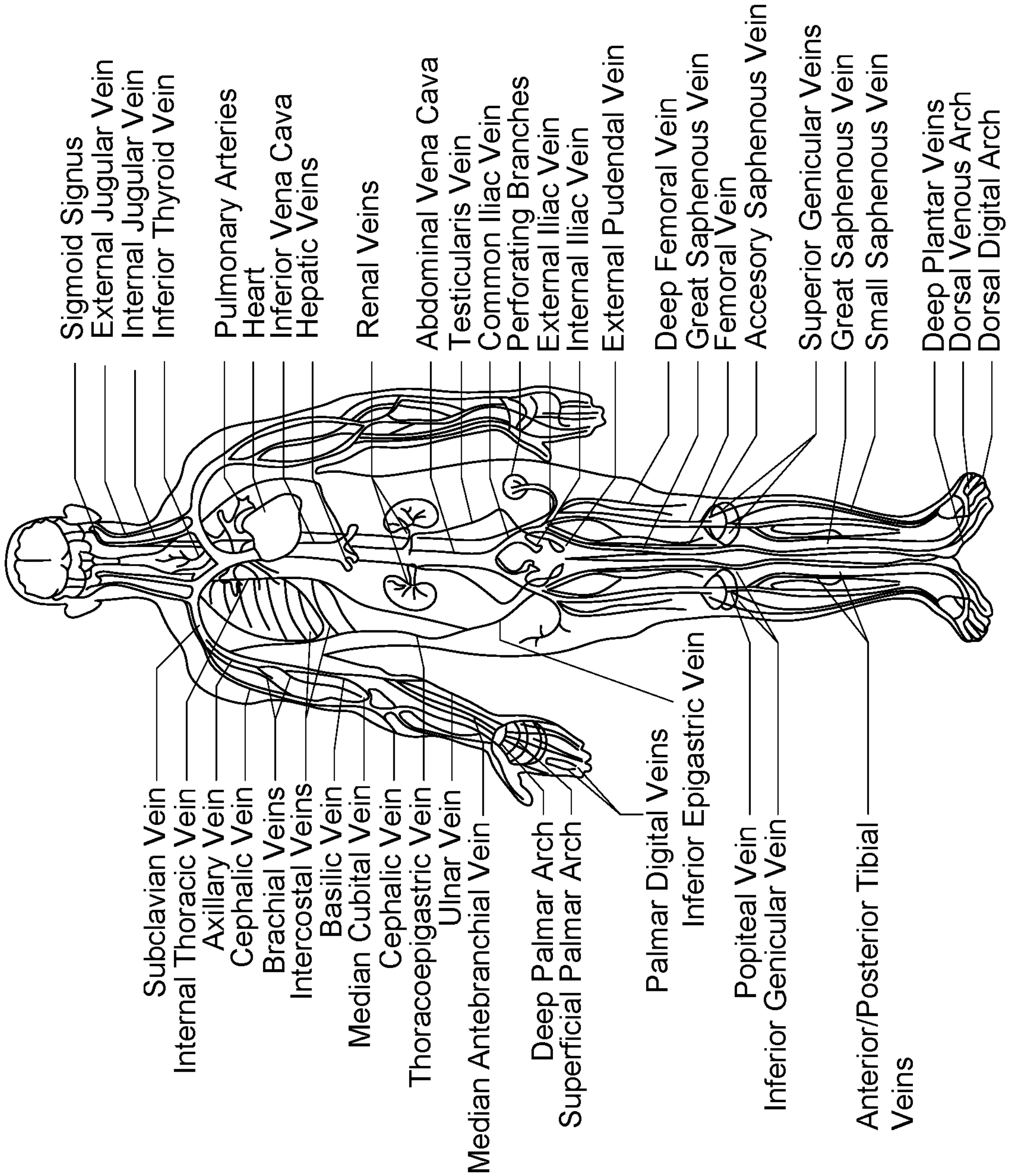
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g., from external vessels), plaque buildup, including without limitation plaque components such as fibrous, fibro-lipidic (fibro fatty), necrotic core, calcified (dense calcium), blood, and/or different stages of thrombus (acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Figure 3:
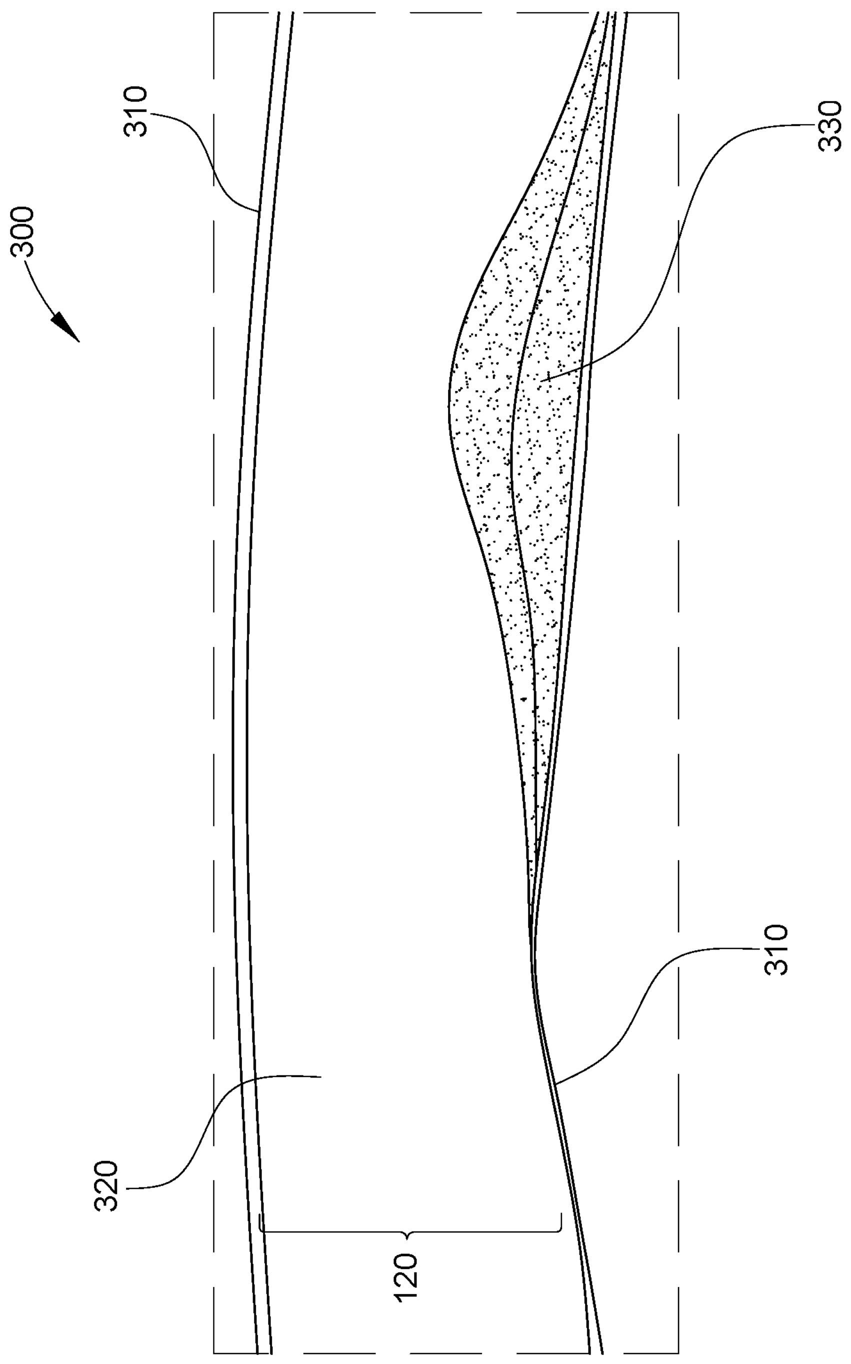
FIG. 3 illustrates a blood vessel incorporating a thrombus.

FIG. 3 illustrates a blood vessel 300 incorporating a thrombus 330. The thrombus occurs between the vessel walls 310 and may restrict the flow of blood 320. Thrombuses come in many types, including sub-acute thrombus, acute thrombus, and chronic thrombus.

Figure 4:
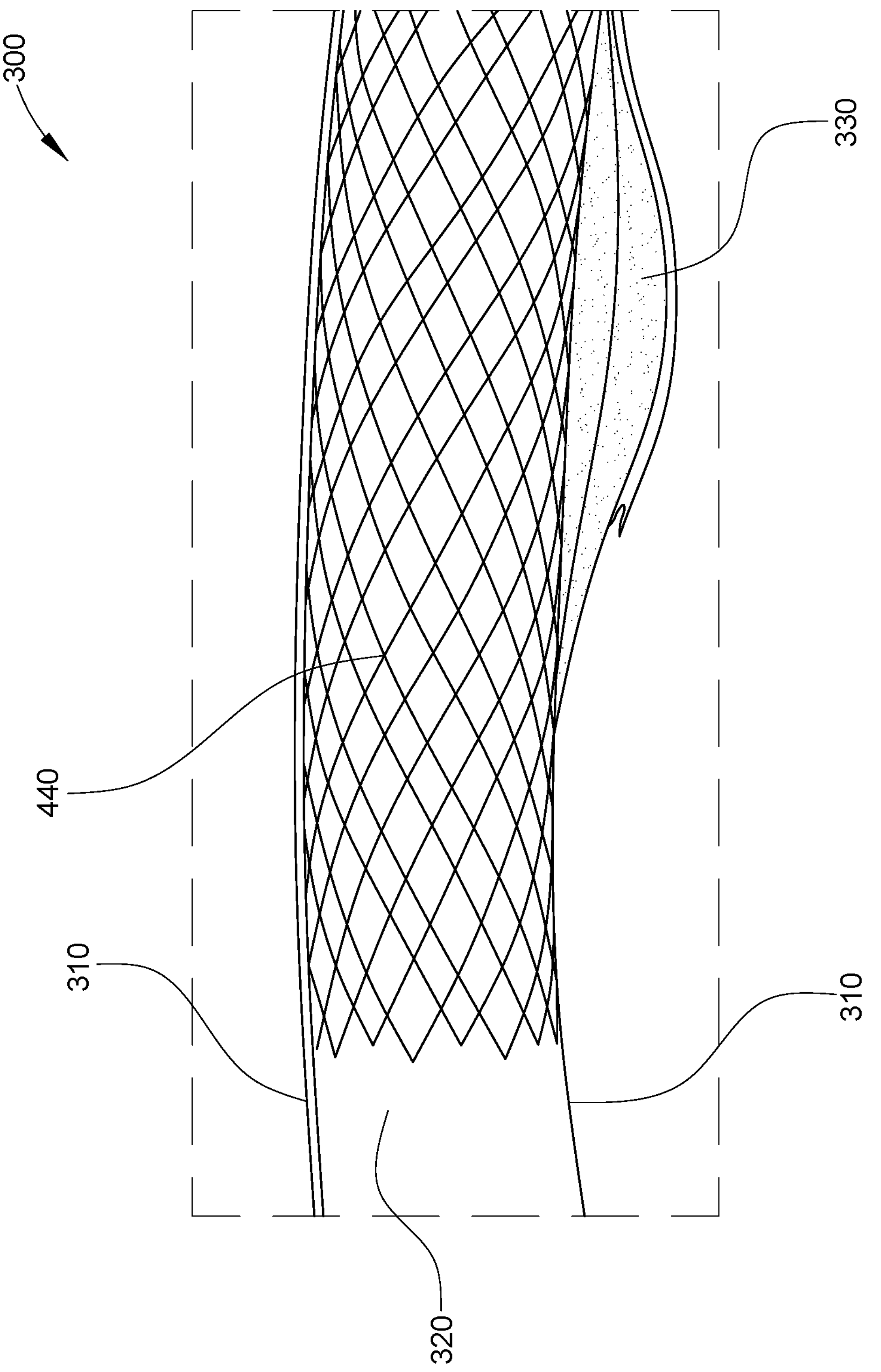
FIG. 4 illustrates a blood vessel incorporating a thrombus and with a stent expanded inside it to restore flow.

FIG. 4 illustrates a blood vessel 300 incorporating a thrombus 330 and with a stent 440 expanded inside it to restore flow. The stent 440 compresses and arrests the thrombus 330, opening the blood vessel 300 and preventing the thrombus 330 from traveling through the blood vessel 300. The stent 440 also pushes the vessel walls 310 outward, thus reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location of the affected area prior to, during, or after treatment.

Figure 5:
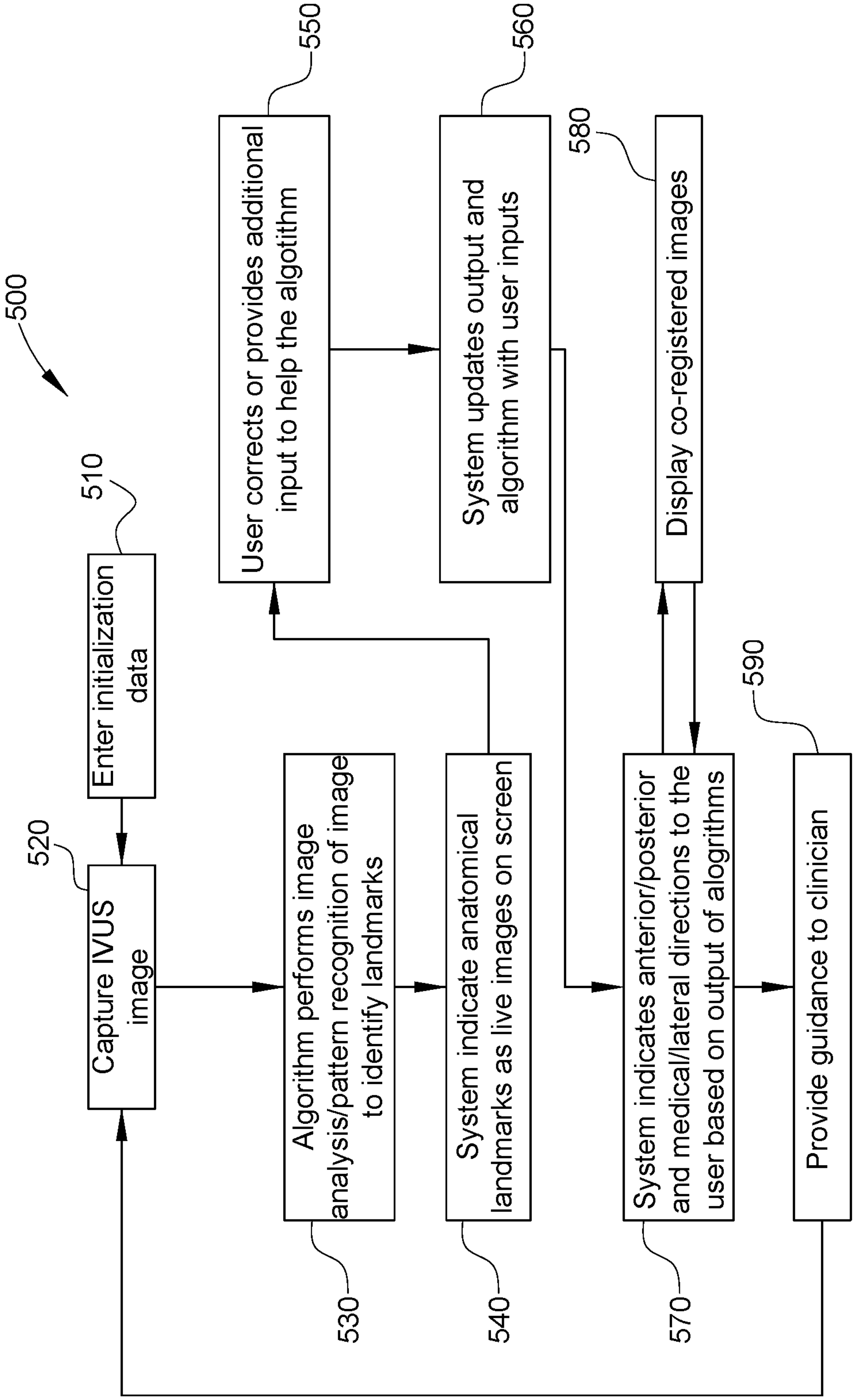
FIG. 5 illustrates a flow diagram for an example intraluminal directional guidance method, in accordance with aspects of the present disclosure.

FIG. 5 illustrates a flow diagram for an example intraluminal directional guidance method 500, in accordance with aspects of the present disclosure. These steps may be executed for example as coded instructions on a processor such as processing system 106 of FIG. 1, and displayed for example on monitor 108 of FIG. 1, in response to inputs by a clinician or other user.

In step 510, the user initializes the intraluminal directional guidance system with directional information at the start of a procedure (e.g., an IVUS pullback procedure). This information may include for example the entry point or access point into the body (e.g., jugular, radial, right or left femoral) and the direction of movement. This information may be used by the system to select specific algorithms, data sets, or body regions for image recognition.

In step 520, the IVUS imaging system 100 captures an IVUS image. Such images may be captured either discretely or continuously during a procedure (e.g., a pullback procedure), and stored within a memory of the processing system 106.

In step 530, the processor 106 performs border detection, image processing, image analysis, and pattern recognition of the captured IVUS image to identify anatomical landmarks (e.g., specific veins, and branching points between veins). While the pullback run is performed, the algorithm detects these landmarks based on a-priori information of the venous system geometry. Such analysis and recognition may rely on conventional techniques, or may be training-based or learning-based (e.g., incorporating machine learning, deep learning, or other related artificial intelligence). In some embodiments, information from external images, when available, may be incorporated into the image recognition algorithm, such that a patient's own unique anatomy is considered. In other embodiments or circumstances, the pattern recognition algorithms may search for analogues of statistically representative anatomy for a given subpopulation, or such statistically representative anatomy may be used to train the algorithm or algorithms.

In step 540, the processor indicates the identified anatomical landmarks to the user, e.g., as annotations or overlays on the live image data displayed on the monitor 108.

In step 550, the processor is receptive to optional additional inputs from the user, comprising information to assist the pattern recognition algorithm. For example, if the user believes the identification displays of step 540 are incorrect, incomplete, mis-located or otherwise in need of correction, the user may optionally correct this information using a keyboard, mouse, joystick, trackball, or other user input device communicatively connected to the processing system 106.

In step 560, if the user has entered such corrections during step 550, the processing system 106 updates both the display on the monitor 108 and the information located within the algorithm to reflect the corrections. Optionally, the processing system 106 may also upload the corrections to a central server, cloud server, or other remote site, such that they may be incorporated into new training sets for machine learning algorithms and then distributed to other users.

In step 570, the processing system 106 determines the orientation of the IVUS image with respect to the patient's body, using the landmarks identified in step 530 or corrected in step 550. For example, the position of a landmark relative to the vessel being imaged, or relative to another landmark, can be used to deduce the orientation of the IVUS image.

The processing system then adds directional indicators to the image on the monitor 108, showing the anterior/posterior and medial/lateral directions on the image. Direction indicators may be relative to the lumen or to absolute space, or may be relative to the patient's body. Optionally, the image may be rotated for example such that the anterior direction (relative to the patient's body) is always facing up on the monitor 108.

Figure 6:
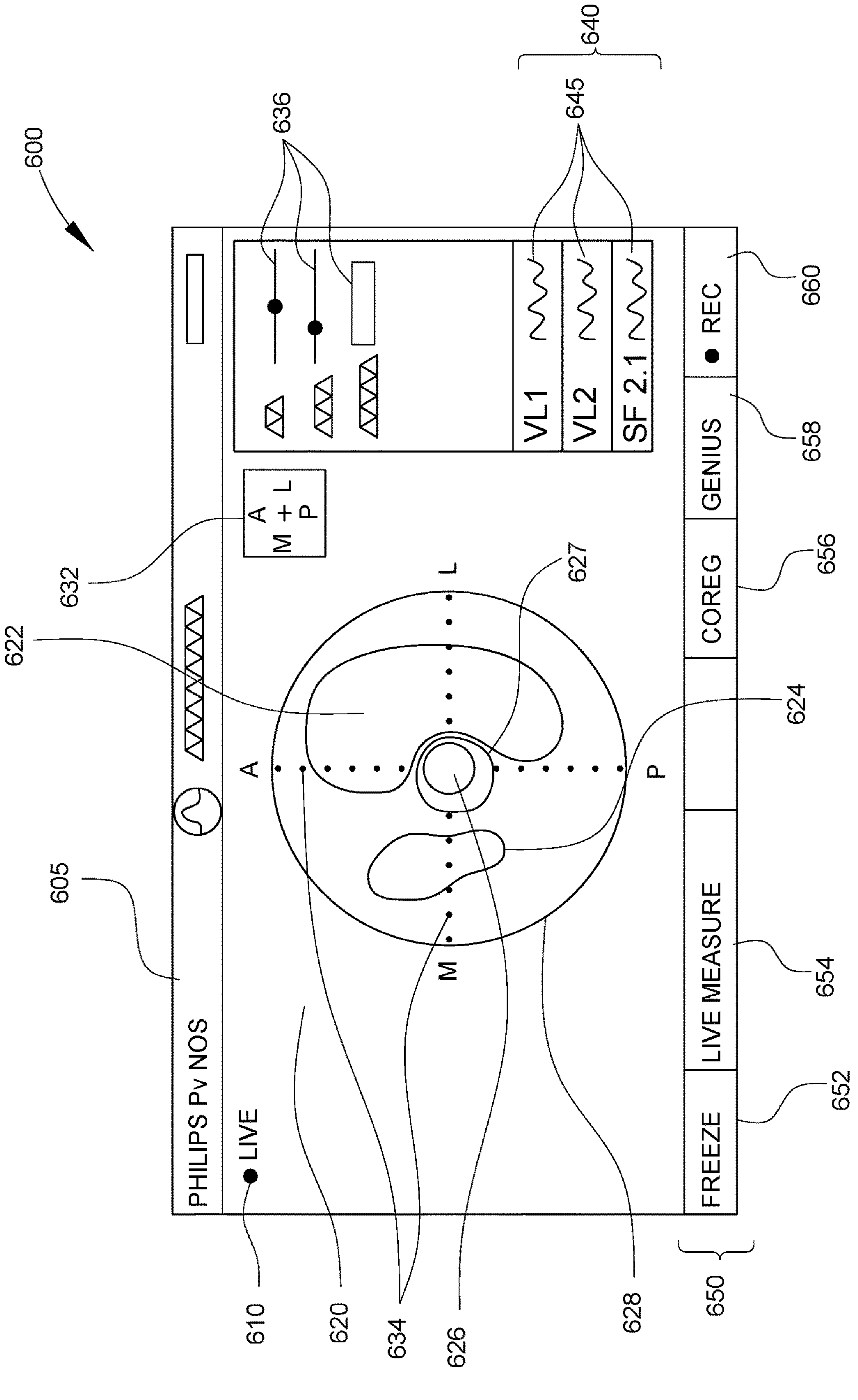
FIG. 6 illustrates a screen display of the intraluminal directional guidance system during live IVUS imaging, according to aspects of the present disclosure.

In step 580, the processing system 106 displays on the display a co-registered image, if available, and if selected to do so by an appropriate user input (e.g., the co-registration button 656 shown in FIG. 6). Such co-registered images may include for example an X-ray, fluoroscopy, CAT scan, external ultrasound, or other image captured by the external imaging system 132 and showing, for example, vasculature or other anatomy in the vicinity of the intravascular imaging probe 102. Aspects of co-registration are described, for example, in U.S. Pat. Nos. 7,930,014 and 8,298,147, the entireties of which are hereby incorporated by reference.

In some embodiments, co-registered images, when available, may also be incorporated into the image recognition algorithm.

In step 590, if an appropriate user input has been selected (e.g., the "genius" control 658), the processing system 106 provides guidance to the clinician regarding movements of the intravascular imaging probe controls 104 that may be required to advance or retract the probe 102 to a desired location within the patient's body. Such guidance may be determined through conventional techniques (e.g., database lookup) or through learning-based techniques.

A person or ordinary skill in the art will understand that for some embodiments, one or more of the above steps could be eliminated or performed in a different sequence, and that other steps may be added. For example, in some embodiments, the system operates in a fully autonomous mode, requiring no input from the user. In some embodiments, the image recognition and landmark identification algorithms incorporate info from external images. In some embodiments, the system allows IVUS to be used by itself, without a need for external images to provide orientation information or clinician roadmaps.

Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

FIG. 6 illustrates a screen display 600 of the intraluminal directional guidance system 500 during live IVUS imaging, such as a peripheral vascular (Pv) venous mode, according to aspects of the present disclosure. Exemplary screen displays or graphical user interfaces (GUIs can be shown on a display of the intraluminal directional guidance system 500, for example, a display of a console, a cart, a bedside controller, a mobile device (e.g., smartphone, tablet, personal digital assistant or PDA), a laptop computer, a desktop computer, etc. The display may be a touchscreen display, and may be in communication with a computer with a processing circuit (e.g., one or more processors and memory). The processing circuit can generate and output the display data to cause the display to show the screen displays of FIGS. 5-7. The computer, processing circuit, and/or processor may also be in communication with a user interface on which user provides inputs. The inputs can be selections of items on the screen displays. The user interface can be a touchscreen display in some instances, or may incorporate a keyboard, a mouse, trackball, stylus, a video-game-style controller with buttons and a joystick, etc.

The screen display 600 of the intraluminal directional guidance system 500 includes a title bar 605, a mode indicator 610, and an intravascular image 620 (e.g., an intravascular ultrasound or IVUS image). The title bar 605 may include useful information such as the trade name and manufacturer name of the intraluminal directional guidance system 500, the current date and time, and other general information as needed. In the example shown in FIG. 6, the mode indicator 610 shows that the system is in "Live" mode. Other possible modes may include but are not limited to "Review", "Playback", "Recording", "Pullback", and "Standby".

The screen display 600 includes a tomographic IVUS image 620 in its central area. In this example, the intravascular imaging probe is located in a lumen 627, and the tomographic image includes a range limit or depth of view circle 628, a circular mask 626 indicating the position of the intravascular imaging probe 102 within the lumen 627, and neighboring anatomical structures 622 and 624, which may for example be adjacent lumens such as veins, arteries, or other branches of the lumen 627. In this example, a small, optional directionality or orientation indicator 632 is provided at the top right corner of the area containing the IVUS image, although it could be provided in other locations and sizes. The directionality indicator is similar to a compass and indicates four directions: anterior ("A"—toward the front of the patient's vody), posterior ("P"—toward the rear of the patient's body), medial ("M"—toward the center of the patient's body), and lateral ("L"—toward the side of the patient's body). A larger directionality or orientation indicator 634 is provided as a graphical overlay on top of the image 620. Through user inputs (e.g., keyboard, mouse, trackball, or joystick inputs), the user can determine the orientation of the IVUS image in the anatomy with reference to the directionality indicator. Alternatively, the computer and/or the processor can rotate the IVUS image automatically, such that for example the anterior direction is always facing up. The orientation of the directionality indicator with respect to the tomographic image 620 is determined by image recognition of identified anatomical landmarks.

In some embodiments, the screen display 600 of the intraluminal directional guidance system 500 also includes image setting controls 636. The user can enhance the intraluminal image or otherwise adjust the display of the intraluminal image (e.g., brightness, contrast, gain, focus, and/or other image settings) using the controls 636, which in this example are located at the top right of the screen display 600, although they could be located in other places or else popped up or pulled down onto the screen via a user input. In some embodiments, the user can access previous image recordings 645 provided in a recording list 640, which in this example is located at the bottom right of the screen display. The previous image recordings 645 may be identified by name (in this example, VL1, VL2, and SF2.1), a date, and/or other identifying information. Various virtual buttons 650 are provided along the bottom of the screen display 600, including a "freeze" button 552 (e.g., to stop live display and freeze the current frame), a "live measure" button 554 (described below with respect to FIG. 7), a "co-registration" button 656 (e.g., to locate the obtain IVUS images on an x-ray image of the vessel), a "genius" or "guidance" or "verbose" mode button 558 (described below with respect to FIG. 8), and "record" button 660 (e.g., to start storing the obtained IVUS data).

Figure 7:
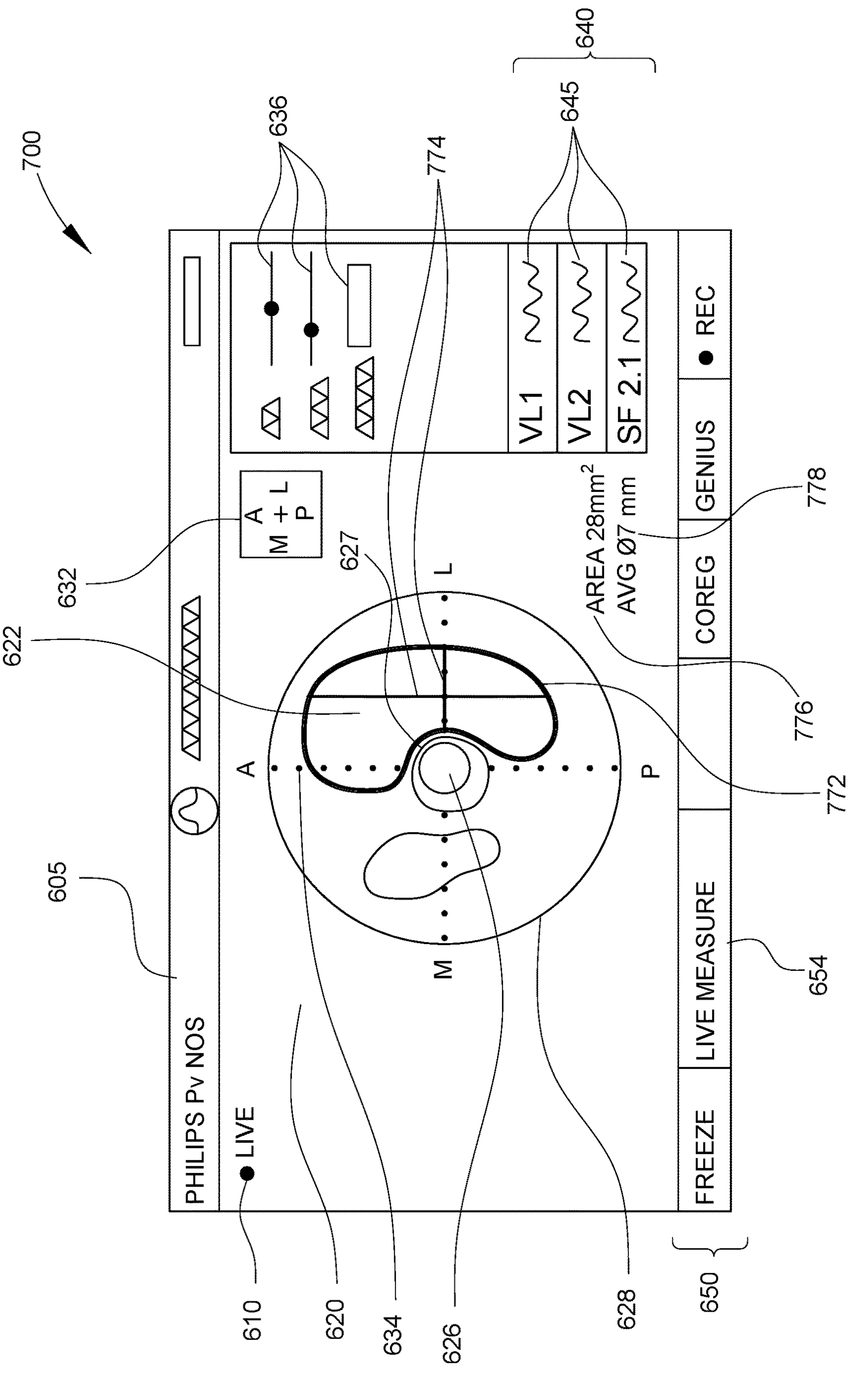
FIG. 7 illustrates a screen display of the intraluminal directional guidance system in accordance with aspects of the present disclosure.

FIG. 7 illustrates a screen display 700 of the intraluminal directional guidance system 500 in accordance with aspects of the present disclosure. The screen display 700 provides live measurements during live IVUS imaging. For example, when the user selects the "live measure" button 654 from the button row 650, the computer and/or processor may execute algorithm(s) to perform image analysis, such as to automatically determine the lumen boundary 772 in the tomographic IVUS image 620 through border identification. The cross-sectional lumen area 776 and/or lumen diameter 778 can be calculated automatically from the lumen boundary. The calculated measurements can be displayed on, e.g., the right side of screen display, adjacent to the IVUS image 620. The measurement may be an average value in some instances (e.g., an average diameter based on two orthogonal cross-sectional diameters 774 of the determined lumen boundary 772, or an average of the largest and smallest detected diameters 774 of the lumen boundary 772). The automatically determined lumen boundary may be highlighted, colored, or shaded on the IVUS image 620. One or more of the automatically determined diameters 774 (e.g., the smallest diameter and the largest diameter) can also be highlighted, colored and/or shaded on the IVUS image. A length can be determined based on a known distance between two images in the sequence, based on a known time between two images in the sequence and a known movement speed for the intraluminal probe 102, or based on recognized landmarks.

Also visible in FIG. 7 are the directionality indicators 632 and 634, probe mask 626, probe range limit or depth of field limit 628, mode indicator 610, image controls 636, and list of stored images 645.

Figure 8:
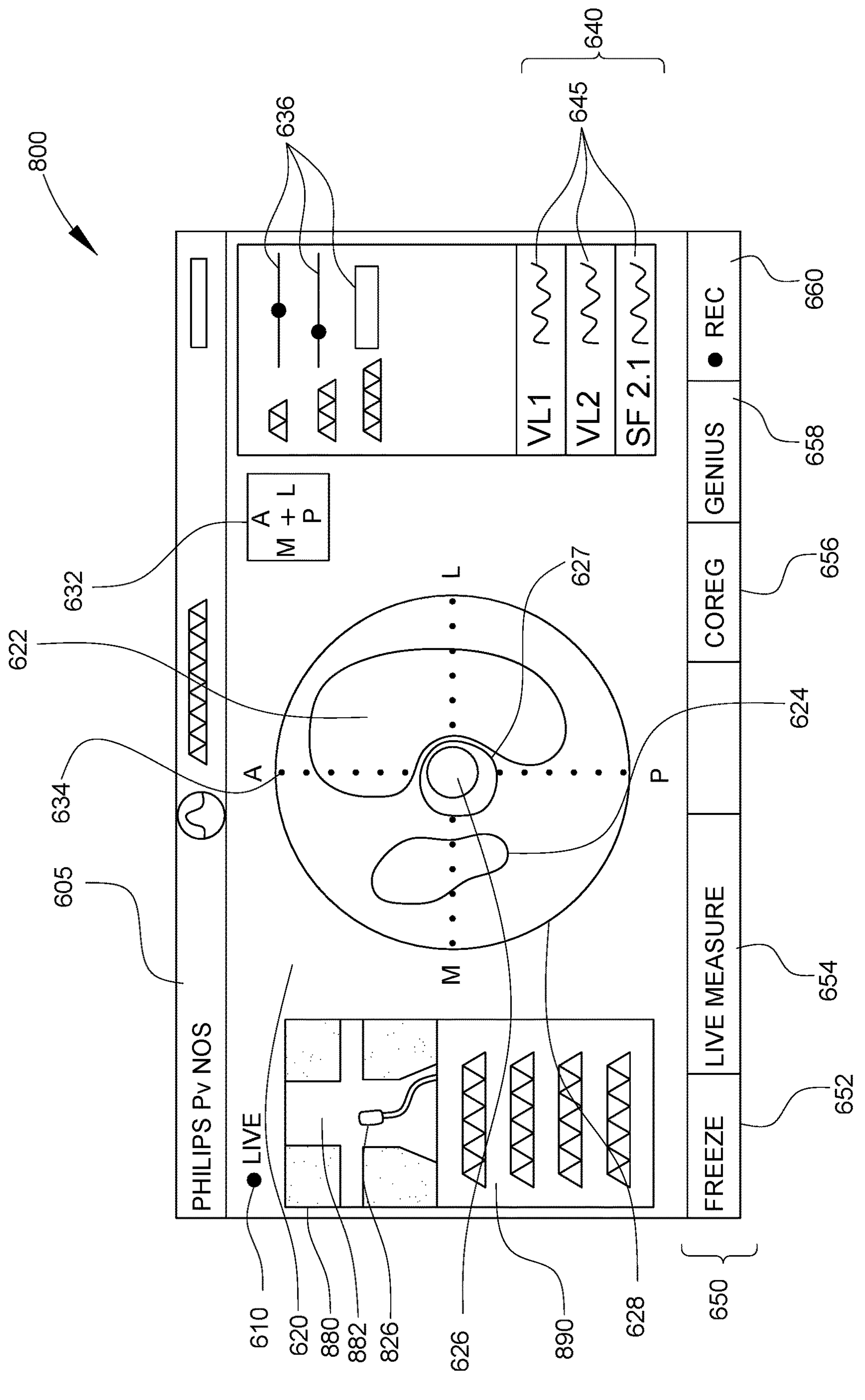
FIG. 8 illustrates a workflow screen display of the intraluminal directional guidance system, in accordance with aspects of the present disclosure.

FIG. 8 illustrates a workflow screen display 800 of the intraluminal directional guidance system 500, in accordance with aspects of the present disclosure. The screen display 800 provides workflow guidance instructions to the user. For example, a user can activate the "genius" or "verbose" or "guidance" button 658 provided on the button row 650 of the workflow screen display 800. Shown here for this example on the top left side of the screen display, a graphical representation 880 of the anatomical structures 882 (e.g., vasculature such as inferior vena cava, abdominal vena cava, renal veins, left and right common iliac veins, left and right common femoral veins, etc.) is displayed for the benefit of the user. Within this graphical representation, a probe representation 826 is also displayed, corresponding to the position of the intravascular imaging probe 102 within the anatomical structures 882. The graphical representation 880 may be an illustration or cartoon of the vasculature or other structures 882, or may be an image such as an X-ray, CT, Mill, or external ultrasound image. For example, the graphical representation 880 may be a roadmap image. The graphical representation can be formed from the obtained IVUS images or other intravascular images, or from an externally acquired view of anatomical structures obtained via the external imaging system 132.

The graphical representation 880 may illustrate the longitudinal extent of the vasculature and can be referenced as a longitudinal display or image longitudinal display (ILD). A graphical representation 826 of the IVUS catheter, including the flexible elongate member positioned within the vasculature and the transducer array at the distal portion of the flexible elongate member, is also displayed within the roadmap image 880. The roadmap image 880 and/or the graphical representation 826 of the catheter/transducer array can be changed as the catheter is moved through different vasculature segments, for example during a pullback procedure.

On the bottom left side of the screen display, written/textual information 890 for the user are provided in a separate instructional pane within the screen display. This information may include but is not limited to status information about the intraluminal directional guidance system 500, instructions for use of the intraluminal directional guidance system 500, and instructions for movement of the intravascular probe 102 within the patient. For example, the information 890 may state, "Genius determines the percentage compression of each segment automatically for you; Move the catheter to the inferior vena cava (IVC); Press record and pullback to the common femoral vein (CFV); Mark the start of each segment." This example is provided for illustrative purposes only and should not be regarded as limiting. Other types of instructions, such as graphical, symbolic, and/or audible, may be provided instead or in addition to those described above.

The computer and/or processor 106 may perform image analysis, using the inputs from the user (e.g., marking the start of each vasculature segment) to automatically calculate the compression percentage (e.g., ratio of actual cross-sectional lumen area and reference cross-sectional lumen area, actual cross-sectional lumen area divided by reference cross-sectional lumen area). The compression percentage for one or more segments of vasculature can for example be shown on the screen display 800.

Figure 9:
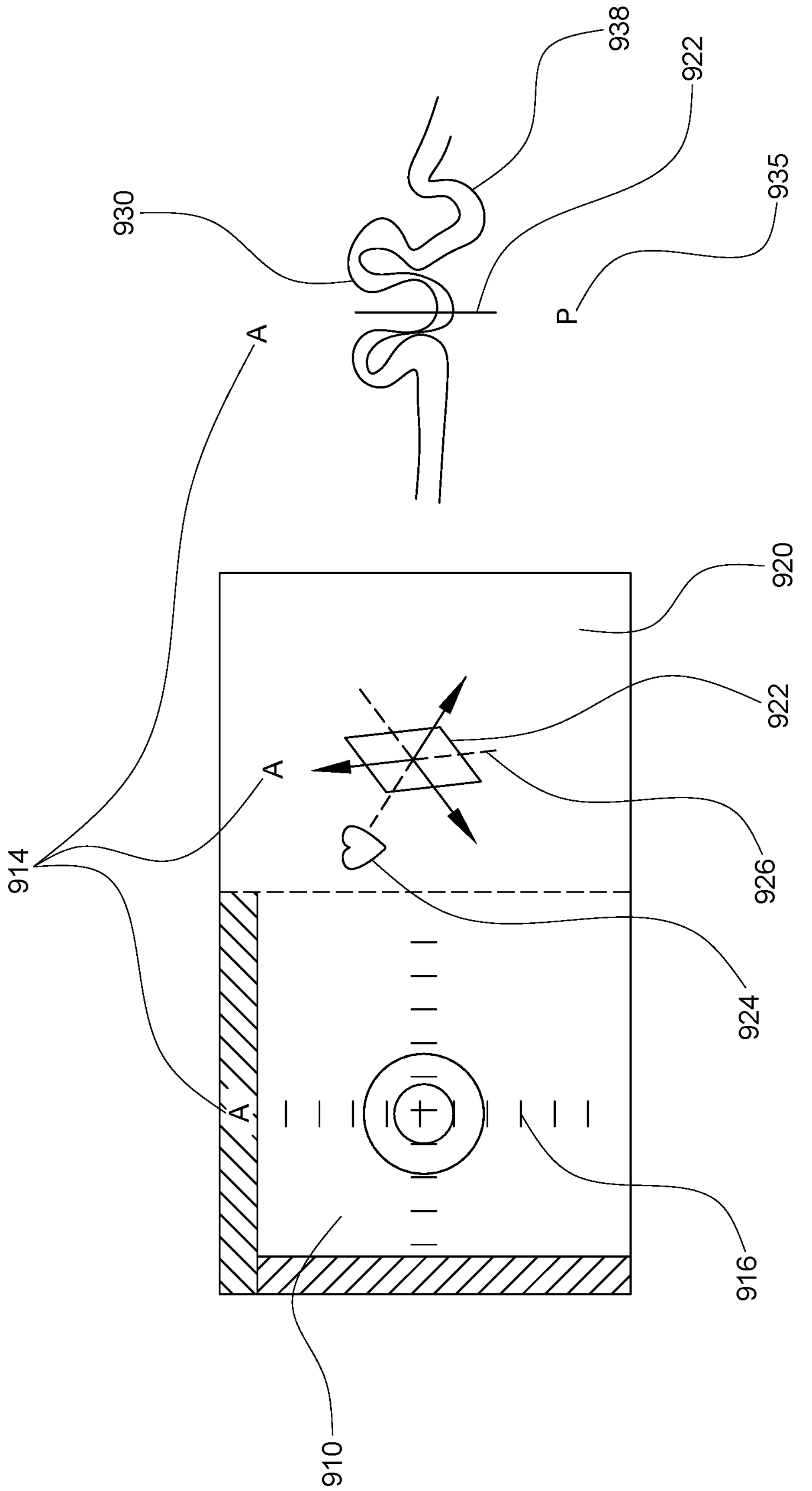
FIG. 9 is an exemplary view of three different visualization types for showing directional information in accordance with at least one embodiment of the present disclosure.

FIG. 9 is an exemplary view of three different visualization types for showing directional information in accordance with at least one embodiment of the present disclosure. Visualization 910 is a cross-sectional or tomographic image, similar to image 620 shown in FIGS. 6-8. In this example, the anterior direction indicator 914 is shown. Direction indicators for the posterior, lateral, and medial directions are not explicitly shown, but may be inferred from reticular indicators 916 superimposed on the image 910. Visualization 920 is a 3D schematic view showing the IVUS imaging plane 922, the anterior direction indicator 914, and an anatomical landmark 924 (e.g., the heart). Direction indicators for the posterior, lateral, and medial directions are not explicitly shown, but may be inferred from axes or compass lines 926 superimposed on the image 920. Visualization 930 is a 3D model of the overall anatomy being imaged, and showing the anterior direction indicator 914, posterior direction indicator 935, anatomical structures 938, and the plane of the IVUS image 922. Medial and lateral direction indicators are not shown explicitly, but may be inferred by a person of ordinary skill as being to the left and right of the image. The anatomical structures 938 (e.g., veins) may be a co-registered image from the external imaging system 132, or may be a stylized or cartoon representation of representative human anatomy.

Stylized can include a figure, diagram, drawing, or graphic that is stored in and retrieved from memory (e.g., common for all patients or representative of all patients), or that is generated from data obtained from one or more IVUS images, and is different than an actual image obtained by an imaging device (e.g., x-ray or IVUS). Other types of visualization may be employed, with the goal of providing directional orientation to the user.

Figure 10:
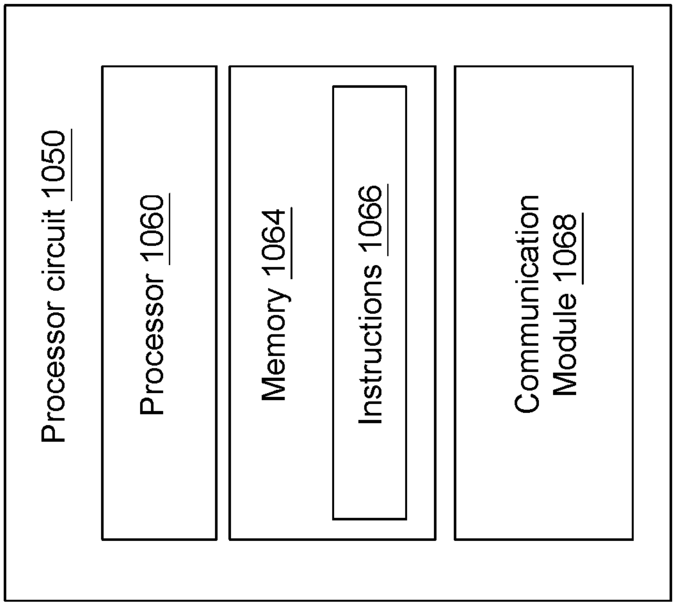
FIG. 10 is a schematic diagram of a processor circuit, according to embodiments of the present disclosure.

FIG. 10 is a schematic diagram of a processor circuit 1050, according to embodiments of the present disclosure. The processor circuit 1050 may be implemented in the ultrasound imaging system 100, or other devices or workstations (e.g., third-party workstations, network routers, etc.), or on a cloud processor or other remote processing unit, as necessary to implement the method. As shown, the processor circuit 1050 may include a processor 1060, a memory 1064, and a communication module 1068. These elements may be in direct or indirect communication with each other, for example via one or more buses.

The processor 1060 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1060 may also comprise another hardware device, a firmware device, or any combination thereof configured to perform the operations described herein. The processor 1060 may also be implemented as a combination of computing devices, e.g., a combination of a DSP and a microprocessor, a plurality of microprocessors, one or more microprocessors in conjunction with a DSP core, or any other such configuration.

The memory 1064 may include a cache memory (e.g., a cache memory of the processor 1060), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1064 includes a non-transitory computer-readable medium. The memory 1064 may store instructions 1066. The instructions 1066 may include instructions that, when executed by the processor 1060, cause the processor 1060 to perform the operations described herein. Instructions 1066 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 1068 can include any electronic circuitry and/or logic circuitry to facilitate direct or indirect communication of data between the processor circuit 1050, and other processors or devices. In that regard, the communication module 1068 can be an input/output (I/O) device. In some instances, the communication module 1068 facilitates direct or indirect communication between various elements of the processor circuit 1050 and/or the ultrasound imaging system 100. The communication module 1068 may communicate within the processor circuit 1050 through numerous methods or protocols. Serial communication protocols may include but are not limited to US SPI, $I^2C$, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the intraluminal directional guidance system may be employed in anatomical systems within the body other than those described, or may be employed to image other disease types, object types, or procedure types than those described. The technology described herein may be applied to intraluminal imaging sensors of diverse types, whether currently in existence or hereinafter developed.

Accordingly, the logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the intraluminal directional guidance system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the intraluminal directional guidance system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intravascular imaging system, comprising:

an intravascular imaging catheter comprising a circular cross-sectional shape and an imaging sensor configured for intravascular ultrasound (IVUS) or optical coherence tomography (OCT), wherein the intravascular imaging catheter is configured to be positioned within a first blood vessel of a patient, wherein an orientation of the intravascular imaging catheter with respect to the patient is unknown; and a processor circuit configured for communication with the intravascular imaging catheter, wherein the processor circuit is configured to:

control the intravascular imaging catheter to obtain a plurality of intravascular images during movement of the intravascular imaging catheter through the first blood vessel, wherein an intravascular image of the plurality of intravascular images is representative of a location along the first blood vessel, wherein an image content of the intravascular image comprises:

the first blood vessel; and an anatomical structure different than the first blood vessel and proximate to the first blood vessel at the location;

determine an orientation with respect to the patient for the intravascular image using image processing on the image content of the intravascular image only, wherein the imaging processing is based on a predetermined geometry between the first blood vessel and the anatomical structure;

output, to a display in communication with the processor circuit, a screen display comprising:

the intravascular image; and a directionality indicator based on the orientation of the intravascular image.

2. The system of claim 1, wherein the processor circuit is configured to output, via the screen display, respective images of the plurality of intravascular images such that each respective intravascular image is rotated in the screen display based on the determined orientation, wherein the directionality indicator comprises the same orientation in the screen display for the respective images of the plurality of intravascular images.

3. The system of claim 1, wherein the screen display further comprises an instructional pane displaying at least one of status information about the system, instructions for operating the system, or instructions for the movement of the intravascular imaging catheter through the blood vessel.

4. The system of claim 1, wherein the blood vessel comprises a tortuous shape such that, during the movement, a direction of the movement changes according to the tortuous shape, and wherein the directionality indicator changes, based on the orientation corresponding to a respective intravascular image of the plurality of intravascular images, wherein the changes in the directionality indicator are a result of the changes in the direction of the movement according to the tortuous shape.

5. The system of claim 1, wherein the directionality indicator further comprises an arrow, line, or pointer.

6. The system of claim 1, wherein the directionality indicator is configured to identify the one or more of the plurality of directions with respect to the patient in relation to an arrangement of the intravascular image in the screen display.

7. The system of claim 1, wherein the processor circuit is configured to identify, within the intravascular image, the first blood vessel and the anatomical structure.

8. The system of claim 1, wherein the anatomical structure comprises at least one of:

a second blood vessel different than the first blood vessel;

a branching between blood vessels; or a ligament.

9. The system of claim 1, further comprising a user interface in communication with the processor circuit, wherein the processor circuit is configured to receive a user input via the user interface.

10. The system of claim 9, wherein the processor circuit is configured to reorient at least one of the intravascular image or the directionality indicator in the screen display, in response to the user input.

11. The system of claim 9, wherein the processor circuit is configured to:

perform an enhancement of the intravascular image, in response to the user input; and modify the intravascular image in the screen display based on the enhancement.

12. The system of claim 11, wherein the enhancement comprises a change to at least one of contrast, gain, focus, or brightness of the intravascular image.

13. The system of claim 1, wherein the processor circuit is configured to:

perform an automatic measurement of the blood vessel based on the intravascular image; and output the automatic measurement via the screen display.

14. The system of claim 13, wherein the automatic measurement comprises at least one of an area, a diameter, a length, or a compression percentage.

15. The system of claim 1, wherein the screen display further comprises:

an external view of the blood vessel.

16. The system of claim 15, wherein the screen display further comprises an indicator identifying a location of the intravascular image along a length of the blood vessel in the external view.

17. The system of claim 1, wherein the intravascular image comprises a circular shape and a representation of the intravascular imaging catheter inside of a circumference of the circular shape, wherein the directionality indicator is positioned outside of the circumference of the circular shape in the screen display.

18. The system of claim 17, wherein the directionality indicator comprises a plurality of alphabetical characters arranged around the outside of the circumference of the circular shape such that the plurality of alphabetical characters point to a corresponding plurality of directions with respect to the patient.

19. The system of claim 18, wherein the plurality of alphabetical characters comprise an "M" representative of a medial direction, an "L" representative of a lateral direction, an "A" representative of an anterior direction, and a "P" representative of a posterior direction.

20. The system of claim 18, wherein the plurality of alphabetical characters is evenly distributed around a perimeter of the intravascular image in the screen display.

21. The system of claim 20, wherein the plurality of alphabetical characters is respectively arranged at a top, a bottom, a left side, and a right side of the intravascular image in the screen display.

22. The system of claim 1, wherein the intravascular imaging catheter is sized and shaped for use in peripheral vasculature such that the first blood vessel comprises a peripheral blood vessel.

23. The system of claim 22, wherein the anatomical structure comprises a second blood vessel different than the first blood vessel, wherein the first blood vessel comprises a peripheral vein, and wherein the second blood vessel comprises a peripheral artery.

24. An intravascular imaging method, comprising:

controlling, with a processor circuit, an intravascular imaging catheter positioned within a blood vessel of a patient to obtain a plurality of intravascular images during movement of the intravascular imaging catheter through the blood vessel, wherein the intravascular imaging catheter comprises a circular cross-sectional shape and an imaging sensor configured for intravascular ultrasound (IVUS) or optical coherence tomography (OCT), wherein an orientation of the intravascular imaging catheter with respect to the patient is unknown, wherein an intravascular image of the plurality of intravascular images is representative of a location along the blood vessel, wherein an image content of the intravascular image comprises:

the blood vessel; and an anatomical structure different than the blood vessel and proximate to the blood vessel at the location;

determining, by the processor circuit, an orientation with respect to the patient for the intravascular image using image processing on the image content of the intravascular image only, wherein the image processing is based on a pre-determined geometry between the blood vessel and the anatomical structure; and outputting, to a display in communication with the processor circuit, a screen display comprising:

the intravascular image; and a directionality indicator based on the orientation of the intravascular image.

* * * * *